United States Patent [19]

Keene

[11] 4,269,178
[45] May 26, 1981

[54] HOOK ASSEMBLY FOR ENGAGING A SPINAL COLUMN

[76] Inventor: James S. Keene, 6305 Keelson Dr., Madison, Wis. 53705

[21] Appl. No.: 45,402

[22] Filed: Jun. 4, 1979

[51] Int. Cl.³ .......................... A61F 5/01; F16B 7/06
[52] U.S. Cl. ................................. 128/69; 128/92 EA; 403/43; 403/342; 24/263 A
[58] Field of Search ............... 128/69, 75, 92 R, 92 B, 128/92 E, 92 EA, 92 EC; 403/43–47, 342, 343, 21; 248/226.1; 24/263 A, 115 M, 68 C, 73 LA, 260

[56] References Cited

U.S. PATENT DOCUMENTS 3,242,922  3/1966  Thomas ........................ 128/92 R

FOREIGN PATENT DOCUMENTS 2649042  1/1978  Fed. Rep. of Germany ......... 128/92 B
2151475  4/1973  France ........................ 128/69
2244446  3/1977  France ........................ 128/69

OTHER PUBLICATIONS

Harrington Spine Instrumentation; Zimmer Catalog 1973-Warsaw, Indiana 46580-p. A-108.
Cotrel; "New Techniques for the Treatment of Idiopathic Scoliosis", Internat'l. Orth., Spring 1978, pp. 247-265.
American Ortomed Corporation Catalog; P.O. Box 3184, Poughkeepsie, N.Y. 12603.

Primary Examiner—Robert W. Michell
Assistant Examiner—Arthur S. Rose
Attorney, Agent, or Firm—Sherman & Shalloway

[57] ABSTRACT

An apparatus used in the treatment of spinal fractures and scoliosis. A threaded rod carries 2 or more sleeves, each sleeve surrounding a portion of the rod and slideable along the entire length of the rod. Each sleeve engages a hook to interconnect the rod with the hook. The hook includes a base for engaging the sleeve. The base has a bore therethrough which receives the sleeve, and a slot is located parallel to and communicating with the bore. The slot has a width which is greater than the diameter of the rod and less than the outside diameter of the sleeve so that the rod can be placed into the slotted base of the hook and held in position by the sleeve which is slipped over the rod and into the bore. A projecting hook portion is integrally connected with the base and is used to engage the bone of the spinal column. A locking system in the form of threaded nuts engages the rod securing the position of the sleeve so that the entire hook assembly may be held in place with respect to the rod. When hooks are faced toward each other on a rod, compression is achieved by advancing the threaded units. Likewise, distraction is achieved by reversing the hooks so as to be facing away from each other. The bore in the base may be tapered or may have a smaller portion to prevent the sleeve from sliding completely through the bore. Opposing openings are located on either side of the base for movement by an instrument, such as a hook holder, to aid in the placement of the hook assembly before interconnection with the threaded rod. Preferably, the hook assembly forms a part of a Harrington compression rod or a tensioning means which interconnects a Harrington distraction rod and a Harrington compression rod.

13 Claims, 8 Drawing Figures

HOOK ASSEMBLY FOR ENGAGING A SPINAL COLUMN

BACKGROUND OF THE INVENTION

1. Field of the Invention

The invention generally relates to a device for the surgical treatment of spinal fractures or for straightening the spine in the surgical treatment for deviations of the spinal column, especially scoliosis. In particular, the present invention relates to a hook assembly for a Harrington compression rod, or a transverse traction device which are affixed to the spine.

2. Description of the Prior Act

Scoliosis is the lateral deviation of the spinal column. The spinal curvature which results from scoliosis is generally defined on the basis of specific reference points. In particular, the extreme upper and lower vertebrae and the most displaced vertebra are of particular interest. The extreme upper and lower vertebrae are those which are the most inclined relative to the median longitudinal axis of the torso. The two planes within which the extreme upper and lower vertebrae can be found define the scoliotic angle. The most displaced vertebra is defined as the vertebra which is the farthest from the median axis of the torso.

When the scoliotic angle of curvature exceeds a given limit of approximately 35°-50°, it becomes necessary to consider surgical treatment of the scoliosis. The surgical treatment is known as arthrodesis and consists of fusing together the vertebrae of the scoliotic curvature, after correcting the scoliotic curvature to the maximum possible extent. Such correction can be accomplished prior to the operation by continuous traction of the spine or by corrective plaster casts.

However, it is during surgery that the correction is completed and finalized. For this purpose, a solid metallic rod with hooks is placed in the concavity of the curvature and a threaded rod with hooks is placed on the convexity of the curvature. These rods straighten the spine and maintain the correction until arthrodesis is attained by means of autogenous bone graft. The implants used most often to correct curvature during surgery are known as the Harrington distraction system and the Harrington compression system, illustrated in FIG. 1.

The distraction system consists of two metallic anchoring devices 116 and 117 of the hook type which are attached to the vertebrae 4 which comprise the spinal column, generally referred to by reference character 1. A notched metal rod 115 serves as a stay and permits the spacing between the hooks 116 and 117. One of the ends 118 of rod 115 is usually notched in such a manner as to permit the distance between anchoring devices 116 and 117 to be adjusted by means of a spreading instrument. Generally, the upper anchoring element 116 is intended for fastening toward the upper end of the spine and is hooked onto a dorsal vertebra 9. Usually, the hook of element 116 is directed upward and shaped in such a manner as to permit its insertion between the articular facets of two adjacent vertebrae. The hook of element 116 penetrates into the interarticular space and is supported on the vertebra.

Similarly, a lower anchoring element 117 is intended to be fastened at the lower end of the spine and is often supported on a lumbar vertebra 10. It is contemplated that the hook associated with element 117 is directed downwardly and supported on the lamina of the lumbar vertebra between the spinous process and the articular facet. In the illustrated example, vertebrae 9 and 10 are considered to be the extreme vertebrae.

The compression system consists of two or more metallic anchoring devices 111 and 112 of the hook type which are attached to selected transverse processes of vertebrae 4 which are situated on the convex side of the scoliotic curvature. Threaded metal rod 113 serves as a stay and permits spacing between the hooks 111 and 112. Hooks 111 and 112 usually face each other and slide freely along threaded rod 113. These hooks are adjusted by means of nuts 114 so as to effect compression of the convexity of the scoliotic curvature. It is understood that more than two hooks and nuts can be used to achieve the desired amount of compression.

Thus, by the application of Harrington distraction and compression systems, the straightening of the scoliotic curvature can be effected and maintained. Vertebral arthrodesis is then achieved by exposing the posterior arches of the vertebrae and attaching autogenous spongy bone with the Harrington devices left in place.

FIG. 2 is an illustration of a patient suffering from scoliosis schematically represented from the rear. The spinal column 1 is visible and indicated schematically by rectangles or trapezoids. The patient illustrated in FIG. 2 exhibits a scoliosis involving a deviation of the vertebrae to the right. The scoliotic curvature can be defined on the basis of the top vertebra 2 and the bottom vertebra 3 of the deviation, and the vertebrae 4 which are located at the peak of the curvature. It is noted that the vertebrae 2 and 3 are those which are most strongly inclined relative to the median longitudinal axis M—M of the body, while vertebrae 4 are those which are farthest from that axis. Angle $\alpha$ is thus a characteristic of the scoliotic curvature. When the angle $\alpha$ exceeds a limit of approximately 35°-50°, it is often necessary to resort to arthrodesis and to install Harrington distraction and compression rod systems, as illustrated in FIG. 1.

However, the Harrington distraction and compression systems are not totally effective in supporting the peak vertebrae 4 which are further away from the axis M—M than the other vertebrae and cannot fully accomplish straightening of the scoliotic curvature. Accordingly, transverse tensioning devices as illustrated in FIGS. 3 and 4 have been suggested by French Pat. No. 2,244,446. Such a transverse tensioning device makes use of (1) a compression rod 11, similar to the Harrington compression rod, and (2) a tensioning element 12. Obviously, the intent of the Harrington distraction rod 5 is to separate the vertebrae apart from each other. The basis of the transverse tensioning device is a tensioning element 12 which is supported by the compression rod 11 on the side of the vertebrae most displaced by the curvature and connected to the other side of the spine by the Harrington distraction rod 5. Preferably, the tensioning means is adjustable so that the peak of the scoliotic curvature can be pulled toward the distraction rod 5, resulting in a better correction of the curvature and a better preservation of the correction obtained. It is contemplated that a transverse tensioning device results in reduction of the lateral displacement of the most displaced vertebrae, completion of the correction obtained by the longitudinal Harrington distraction rod, and relief of the load on the supporting vertebrae.

Generally, the transverse tensioning devices of the prior art have been comprised of compression rod 11 and tensioning element 12, the first of which is intended to be supported on two vertebrae 4 which are closest to the peak of the scoliotic curvature, and the second of which permits the first to be brought nearer to the metallic distraction rod 5.

Compression rod 11 is generally comprised of a threaded rod 13, at one end of which is permanently fastened a hook 14. This rod 13 passes freely through another hook 15 which is held in place by nuts 16. Hook 15 slides along rod 13 and faces hook 14. Hook 14 has a rounded and beveled end 17 which allows it to be supported, from top to bottom, by the transverse processes of the upper vertebra 4 of the peak, after cutting of the costotransverse ligament. Hook 15 passes from the bottom to top beneath the transverse process of the lower vertebra 4 of the peak. Nut and locking nut 16 permit hooks 14 and 15 to be brought closer to each other and to be tightened in such a way as to effect a firm transverse grip. Hook 15 is finally locked into position by means of a set screw S which jams the threads of rod 11. Hooks 14 and 15 are attached to the transverse processes of vertebra 4 which are situated on the convex side of the scoliotic curvature.

Tensioning element 12 comprises a threaded rod having one end which is permanently fastened to hook 18. The rod passes freely through another hook 19 which is held in place on the rod by nuts 21. Hook 19 is able to slide along the rod and faces hook 18. Hook 18 engages rod 13 and hook 19 engages Harrington rod 5. By screwing nut and locking nut 20 along the rod hooks 18 and 19 approach each other and the peak vertebrae 4 are made to approach median axis M—M. This allows better correction of the scoliotic curvature. Hook 19 is finally locked into position by means of a set screws which jam the threads of element 12. It is noted that elements 11 and 12 are located at the posterior side of the spine, element 12 being in contact with the spongy graft 21 necessary for this arthrodesis so as to reinforce the solidity of the arthrodesis.

The surgical techniques used in employing the transverse traction device illustrated in FIGS. 3 and 4 are outlined in more detail by Dr. Cotrel in his article entitled "New Techniques for the Treatment of Idiopathic Scoliosis," *International Orthopedics,* Spring, 1978, pp. 247-265.

The basic problems with the above described transverse traction system are as follows:

1. It is difficult to apply.
2. It requires the use of additional instruments other than those commonly available to spinal surgeons familiar with the Harrington procedure.
3. It provides for the use of tiny set screws to positively locate hooks 15 and 19 on elements 11 and 12. Such set screws must be cut off flush with the hooks, thereby risking the loss of a portion of a set screw in the human body.
4. Hook 18 of element 12 does not positively locate on element 11 and is subject to slippage.

SUMMARY OF THE INVENTION

It is an object of this invention to provide a hook assembly for use with a threaded Harrington compression rod which may be used for the treatment of scoliosis or spinal fractures, the hook assembly allowing a single surgeon to easily place the Harrington rod in position.

It is a further object of this invention to provide a hook assembly for a threaded Harrington compression rod which allows the hooks to be properly spaced on the Harrington rod.

It is a further object of this invention to provide a hook assembly for a Harrington compression rod which allows the hooks to be tilted and manipulated into position before engaging the rod and being retained on the rod.

It is another object of this invention to describe a hook assembly for use in combination with a Harrington compression rod which obviates the need for a partial laminectomy, when hooks are being placed on the laminae.

It is a further object of this invention to provide a hook assembly for use with a Harrington compression rod which has a radiused shoe on each hook which can be placed to clear the edge of the lamina before the rod is tightened to achieve compression or distraction.

It is another object of this invention to describe a hook assembly for use with a Harrington distraction rod, a Harrington compression rod or a tensioning device interconnecting such rods which includes a hook comprised of a base and projecting hook, the base having a bore therethrough for receiving a sleeve located on the rod.

It is yet another object of this invention to provide a hook assembly for a Harrington compression rod which allows the preliminary placement of the hook before engaging the rod.

It is a final object of the hook assembly of this invention to provide a system for use in combination with a Harrington compression rod which significantly reduces the surgical time required for installing such rods.

The basis of the invention is a hook assembly for use with a threaded rod to inter-engage the threaded rod with a portion of the spinal column. The hook assembly includes a sleeve or bushing for engaging the threaded rod and surrounding a portion thereof. The sleeve or bushing is slidable along the length of the rod. A base engages the sleeve and has a bore therethrough for receiving the sleeve. The base has a first and second end and the bore in the base extends from the first end to the second end of the base. A slot is provided in the base on the side or top thereof and is parallel to and communicates with the bore. The slot has a width which is greater than the diameter of the threaded rod so that the threaded rod may pass therethrough and less than the outside diameter of the sleeve so that the sleeve does not pass therethrough. A hook or shoe is integrally connected to and projects from the base. A locking system is employed to position the hook assembly with respect to the threaded rod so that the relative position of the hook assembly will remain consistent with respect to the threaded rod. The locking system cooperates with and is independently moveable relative to the base and relative to the sleeve or bushing and along the rod for engaging the rod and locking the base with respect to the rod. In a preferred embodiment, the locking system is a threaded nut which engages the threaded rod on one side of the sleeve and base. The threaded nut has a width greater than the inner diameter of the sleeve or bushing. It is contemplated that one of the threaded nuts may be integrally attached to the sleeve to facilitate placement of the sleeve. Means are provided for preventing the sleeve or bushing from sliding out of the base through the second end when said sleeve or bushing is received within the bore through the first end. For example, the means for preventing the sleeve or bushing from sliding out of the bore comprises the bore in the base being tapered. The bore in the base may be tapered so that the bore engages the sleeve and the sleeve does not completely pass therethrough. An example of an alternate means for preventing the sleeve or bushing from sliding out of the bore comprises a portion of the bore in the base having a diameter which is less than the outside diameter of the sleeve or bushing, thereby forming a shoulder against which the sleeve or bushing abuts. That is the bore may have a smaller diameter portion which prevents passage of the sleeve completely therethrough. In addition, the base may be provided with opposing openings for engagement by an instrument, such as a hook holder.

In use, each base and hook are placed on the spinal column and the rod is positioned within the slot of each hook. The sleeve or bushing is then located within the bore in the base to secure the rod to the hook. The threaded nut is then turned down to achieve compression or distraction, and the entire hook assembly is held in position.

BRIEF DESCRIPTION OF THE DRAWINGS

These features and objects of the invention, as well as others, will become apparent to those skilled in the art by referring to the accompanying drawings in which.

DETAILED DESCRIPTION OF THE INVENTION

The basic feature of the invention is the connecting means which forms the hook assembly as illustrated in FIGS. 5-8. This hook assembly allows the placement of the hook with engagement of the spinal column before the hook and attached base are connected to the threaded rod. The hook assembly further provides a positive interconnection between the base and hook portions and the threaded rod so that, in the locked position, pivoting or other movement between the threaded rod and base of the hook assembly is not possible.

Figure 1:
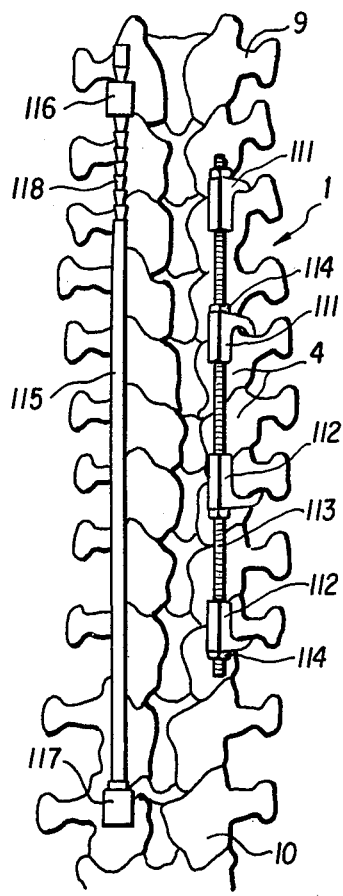
FIG. 1 is an illustration of a Harrington distraction rod and a Harrington compression rod engaging the spinal column.
Figure 2:
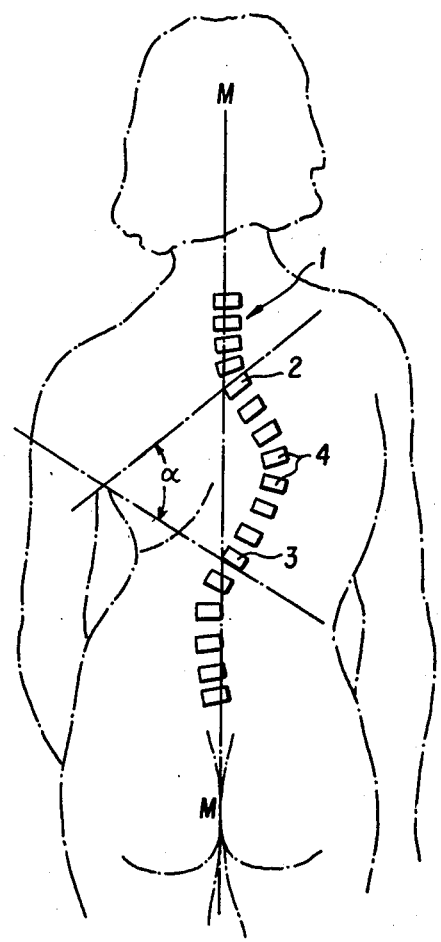
FIG. 2 is a schematic illustration, from the rear, of an individual suffering from scoliotic curvature of the spinal column.
Figure 3:
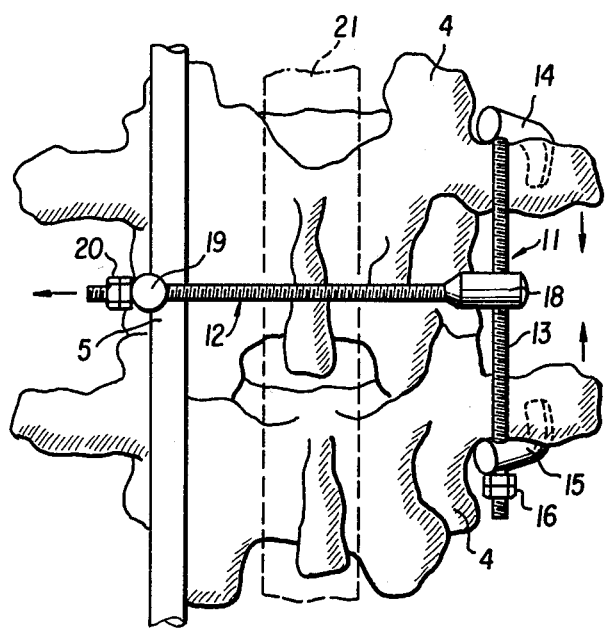
FIG. 3 shows a Cotrel compression rod and a Harrington distraction rod engaging the spinal column and tensioned by a device disclosed in French Pat. No. 2,244,466.
Figure 4:
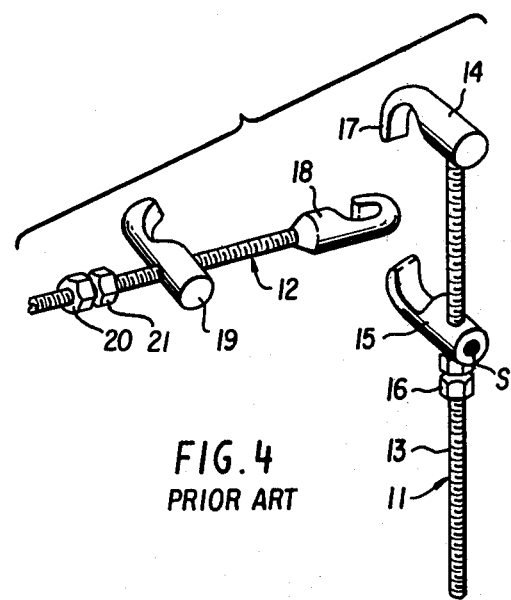
Figure 5:
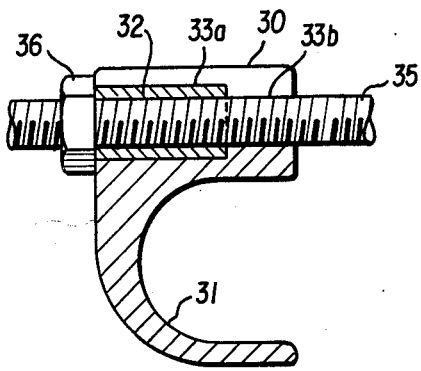
FIG. 5 is a cross-sectional view of the hook assembly of the invention shown in the locked position.

Referring in more detail to the features of FIG. 5, it can be appreciated that threaded rod 35 is somewhat similar to rod 113 shown in FIG. 1. In particular, rod 35 is a threaded rod which interconnects two or more hook means for engaging the spinal column or interengaging a Harrington compression rod and a Harrington distraction rod. It is, therefore, noted that the hook assembly of the invention may be used as a part of a distraction rod, as part of a compression rod or as part of a tensioning means which interconnects a Harrington distraction rod and a Harrington compression rod. In fact, the hook assembly may be used on any surgical system in which engagement of a hook means is required.

Figure 6:
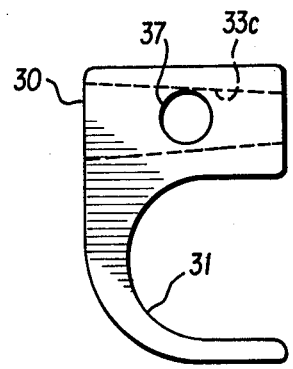
FIG. 6 is a side view of the hook and base portions of the hook assembly.

The threaded rod 35 carries a sleeve 32 which surrounds the rod and slides along the rod for free positioning. The base portion 30 of the hook assembly is integrally connected to a hook portion 31 which particularly engages the spinal column or rod which is to be the anchoring means. Bore 33a is longitudinally located within the base portion 30 and is sized to accept the sleeve 32. Bore 33b is provided and has a diameter which is less than the outside diameter of the sleeve 32 so that the sleeve is prevented from completely passing through bore 33a and through the base portion 30 of the hook assembly. Alternatively, as shown in FIG. 6, the bore within the base portion 30 may be tapered bore 33c which performs the same function as bores 33a and 33b.

Figure 7:
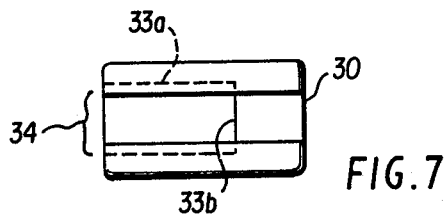
FIG. 7 is a sectional view of the base of the hook assembly taken along lines 7—7 of FIG. 5.
Figure 8:
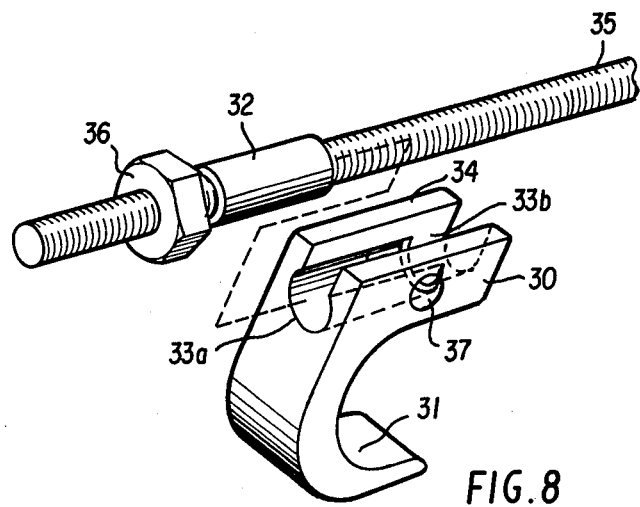
FIG. 8 is a perspective view showing the hook assembly in position to be engaged.

A slot 34, as best shown in FIGS. 7 and 8, is parallel to the bore 33a and in communication with the bore 33a to form an opening in the base 30. The size of the slot 34 in relation to the sleeve 32 and threaded rod 35 forms a critical feature of the invention. In the preferred embodiment, the slot 34 should form an opening within the base 30 so that the width of slot 34 is greater than the diameter of rod 35 but less than the outside diameter of sleeve 32. The result of this critical dimension is that the slot 34 allows the rod 35 to be slipped into the hook assembly and then the sleeve 31 is moved along the rod 35 to engage the hook assembly. This movement can be appreciated by referring to the dotted lines in FIG. 8. Once the base 30 is in position around the sleeve 32 so that the sleeve 32 is located within bore 33a and abuts the shoulder between bore 33a and 33b, locking nuts 36 may be turned to lock the position of sleeve 32, base portion 30 and integrally connected hook portion 31 into position with respect to the threaded rod 35.

In an alternative embodiment, it is contemplated that the sleeve 32 may be integrally connected to a locking nut 36 so that the particular position of the sleeve 32 is determined by the position of the locking nut to which it is connected. In some operations, this type of structure allows for the manipulation of the hook assembly in a more efficient fashion.

It is further contemplated that the base portion 30 of the hook assembly may be provided with engaging openings 37. These openings, which are opposing, are provided so that the entire base portion 30 and integrally connected hook portion 31 may be handled by a hook holder, hemostat or other convenient device. These engaging openings are especially necessary when the apparatus being implanted is of an extremely small nature and manipulation of the base portion 30 and integrally connected hook portion 31 becomes difficult with human fingers. It is also contemplated that other engaging means, not shown, may be provided on the base portion 31, such as notches, multiple openings, transverse bores, projections or protrusions.

It is, therefore, apparent that the hook assembly allows for the engagement of the hook portion 31 by manipulation of the base portion 30 before the base portion is slideably engaged by the sleeve 32 carried by the threaded rod 35. With the hook portion 31 engaged to an anchor, such as the spinal column, the threaded rod 35 may be slipped through the slot 34 and the sleeve 32 is then moved along the threaded rod 35 into the bore 33a. With the threaded rod 35 and sleeve 32 in place, the entire hook assembly is retained on the rod 35 by locking nut 36 and compression or distraction may be achieved by advancing the locking nut in the proper direction. This allows the surgeon to place each hook on the spine, tilting or manipulating the hook as required to achieve a good purchase. This often avoids the partial laminectomy that is sometimes necessary with the Harrington systems of the prior art.

Use of the hook assembly apparatus as described above for the treatment of spinal fracture as compared with the prior art devices has shown that a thirty to forty minute reduction in surgical time can be achieved when operating on fracture cases. It is contemplated that even more time could be saved in the performance of scoliosis cases.

Various changes may be made to the details of the invention, as disclosed, without sacrificing the advantages thereof or departing from the scope of the appended claims. For example, any hook style may be adapted to this design or the sleeve or bushing employed can have a square, hexagonal or other shape. It is only necessary that the internal shape of the sleeve be complementary and corresponding to the external shape of the threaded rod and that the external shape of the sleeve be equivalent to or complementary with the internal shape of the bore and the base.

Furthermore, although the present invention has been disclosed and discussed with particular regard to its exceptional advantages in terms of devices for the treatment of spinal fracture and scoliosis, it may be understood that the invention may be employed in several surgical as well as industrial applications wherein a rod engages a portion by means of a hook which requires manipulation about the portion. In addition, although the preferred embodiment contemplates a metallic structure, the invention may be comprised of any suitable form-retaining material.

What is claimed is:

1. An apparatus for engaging a second device including a second rod, a bone or a portion of a spinal column, said apparatus comprising:
   (a) a rod;
   (b) a sleeve means slidable along the length of said rod for engaging said rod;
   (c) base means having a first and second end for engaging said sleeve means and having a bore extending therethrough from said first end to said second end for receiving said sleeve means; said base means having a slot parallel with and communicating with said bore, said slot having a width which is greater than the diameter of said rod and less than the outside diameter of the sleeve means;
   (d) means for preventing said sleeve means from sliding out of said bore through said second end when said sleeve means is received within said bore through said first end;
   (e) hook means connected to and projecting from said base means; and
   (f) locking means cooperating with and independently moveable relative to said base means and said sleeve means and along said rod for engaging said rod, said locking means having a width greater than the inner diameter of said sleeve means.

2. The apparatus of claim 1 wherein the means for preventing said sleeve means from sliding out of said bore comprises the bore in said base means being tapered.

3. The apparatus of claim 1 wherein said rod is threaded and said locking means comprises at least one threaded nut for engaging said rod and said base means.

4. The apparatus of claim 1 wherein said rod is threaded and said locking means comprises a pair of threaded nuts for engaging said rod on one side of the base means and sleeve means.

5. The apparatus of claim 1 wherein said base means further includes an opening for engagement by an instrument.

6. An apparatus for engaging a second device including a rod, a bone or a portion of a spinal column, said apparatus comprising:
   (a) a rod;
   (b) a sleeve means freely slidable along the length of said rod for engaging said rod;
   (c) base means having a first and second end for engaging said sleeve means and having a bore extending therethrough from said first end to said second end for receiving said sleeve means; said base means having a slot parallel with and communicating with said bore, said slot having a width which is greater than a diameter of said rod and less than the outside diameter of the sleeve means;
   (d) means for preventing said sleeve means from sliding out of said bore through said second end when said sleeve means is received within said bore through said first end, said means comprising the bore in said base means having a portion of the diameter of the bore which is less than the outside diameter of the sleeve means;
   (e) hook means connected to and projecting from said base means; and
   (f) locking means cooperating with and independently moveable relative to said base means and said sleeve means and along said threaded rod for engaging said rod, said locking means having a width greater than the inner diameter of said sleeve means.

7. The apparatus of claim 6 wherein said rod is threaded and said locking means comprises at least one threaded nut for engaging the said rod and said base means.

8. The apparatus of claim 6 wherein said base means further includes an opening for engagement by an instrument.

9. An apparatus for engaging a spinal column comprising:
   (a) a threaded rod;
   (b) a bushing surrounding a portion of the threaded rod and slidable on said rod for engaging said rod;
   (c) a base having a first and second end for engaging the bushing and having a bore extending therethrough from said first end to said second end for receiving the bushing; said base having a slot parallel with and communicating with the bore, said slot having a width which is greater than the diameter of said rod and less than the outside diameter of the bushing;
   (d) means for preventing said bushing from sliding out of said bore through said second end when said bushing is received within said bore through said first end; and
   (e) a hook connected to and projecting from the base;
   (f) locking means cooperating with and independently moveable relative to said base and said bushing and along said threaded rod for engaging said rod, said locking means comprising at least one threaded nut and said nut having a width greater than the inner diameter of said bushing.

10. The apparatus of claim 9 wherein the means for preventing said bushing from sliding out of said bore comprises the bore in said base being tapered.

11. The apparatus of claim 9 wherein said locking means comprises a pair of threaded nuts for engaging the rod on one side of the base and bushing.

12. An apparatus for engaging a spinal column comprising:
(a) a threaded rod;
(b) a bushing surrounding a portion of the threaded rod and slidable on said rod for engaging said rod;
(c) a base having a first and second end for engaging the bushing and having a bore extending therethrough from said first end to said second end for receiving the bushing; said base having a slot parallel with and communicating with the bore, said slot having a width which is greater then the diameter of the rod and less than the outside diameter of the bushing;
(d) means for preventing said bushing from sliding out of said bore through said second end when said bushing is received within said bore through said first end, said means comprising the bore in said base having a portion of the diameter of the bore which is less than the outside diameter of the bushing; thereby forming a shoulder against which the bushing abuts;
(e) a hook connected to and projecting from the base; and
(f) locking means cooperating with and independently moveable relative to said base and said bushing and along said threaded rod for engaging said rod, said locking means comprising at least one threaded nut and said nut having a width greater than the inner diameter of said bushing.

13. The apparatus of claim 12 wherein said locking means comprises a pair of threaded nuts for engaging the said rod on one side of the base and bushing.

* * * * *